United States Patent
Qazi et al.

(10) Patent No.: US 6,989,162 B2
(45) Date of Patent: Jan. 24, 2006

(54) HEPATOPROTECTIVE AGENT OF PLANT ORIGIN AND A PROCESS THEREOF

(75) Inventors: Ghulam Nabi Qazi, Jammu (IN); Om Parkash Suri, Jammu (IN); Kasturi Lal Bedi, Jammu (IN); Krishan Avtar Suri, Jammu (IN); Bishan Datt Gupta, Jammu (IN); Bupinder Singh Jaggi, Jammu (IN); Bal Krishan Kapahi, Jammu (IN); Naresh Kumar Satti, Jammu (IN); Musarat Amina, Jammu (IN); Bal Krishan Chandan, Jammu (IN); Neelam Sharma, Jammu (IN); Gurdarshan Singh, Jammu (IN)

(73) Assignee: Council of Scientific & Industrial Research (IN)

(*) Notice: Subject to any disclaimer, the term of this patent is extended or adjusted under 35 U.S.C. 154(b) by 43 days.

(21) Appl. No.: 10/403,700

(22) Filed: Mar. 31, 2003

(65) Prior Publication Data

US 2004/0192619 A1 Sep. 30, 2004

(51) Int. Cl.
  A61K 35/78 (2006.01)
  A61K 31/70 (2006.01)
  A61K 31/33 (2006.01)
  A61K 31/555 (2006.01)
  A61K 31/05 (2006.01)

(52) U.S. Cl. .......... 424/725; 514/25; 514/183; 514/185; 514/732; 514/893

(58) Field of Classification Search .......... 424/725; 514/25, 183, 185, 732, 893
See application file for complete search history.

(56) References Cited

U.S. PATENT DOCUMENTS 5,719,129 A * 2/1998 Andary et al. .......... 514/25

OTHER PUBLICATIONS

Xiong et al. Life Sci. 1999. vol. 65, No. 4, pp. 421–430.*
Yim et al. Saengyal Hakhoechi. 1997. vol. 28, No. 4, pp. 252–256, CAPLUS Abstract enclosed.*

Ahmad et al., "Flavones from *Colebrookia oppositifolia*", Indian Journal of Chemistry, vol. 12, pp. 1327–1328 (1974).
Andary, et al., "Structures of Verbascoside and Orobancho-side, Caffeic Acid Sugar Esters from Orobanche Rapum–Genistae", Phytochemistry, vol. 21, pp. 1123–1127 (1982).
Gupta et al., "Antifertility studies of *Colebrookia oppositifolia* leaf extract in male rats with special reference to testicular cell population dynamics", Fitoterapia, vol. 72, pp. 236–245 (2001).
Houghton et al., "Anti–Hepatotoxic Activity of Extracts and Constituents of Buddleja Species", Planta Medica, Journal of Medicinal Plant Research, vol. 55, pp. 123–126 (1989).
Patwardhan et al., "Two New Flavones from *Colebrookea oppositifolia*", Indian Journal of Chemistry, vol. 20B, p. 627 (1981).
Quanbo Xing, et al., "Hepatoprotective Activity of Phenylethanoids from *Cistanche deserticola*", Planta Medica, vol. 64, pp. 120–125 (1998).
Yang et al, "Flavonoid Glycosides from *Colebrookea oppositifolia*", Phytochemistry, vol. 42, pp. 867–869 (1996).

* cited by examiner

Primary Examiner—Christopher R. Tate
(74) Attorney, Agent, or Firm—Fish & Richardson, PC

(57) ABSTRACT

A process of isolation of pure Acteoside of high hepatoprotection from plant *Colerbrookea oppositifolia*, said process comprising steps of drying aerial parts of the plant, grounding the dried parts into powder, percolating the powder with water or ethanol for 3–4 times to obtain an extract, filtering the extract for clearing of suspended particles to obtain supernatant, drying the supernatant at about 45 to 55° C. to obtain a residue, fractionating the residue with chloroform, ethyl acetate, and butanol successively, subjecting butanol fraction to adsorption chromatography of $SiO_2$ after adding methanol to the fraction, charging the adsorbed fraction to glass column, eluting the column with solvents of increasing polarity of methanol:chloroform to obtain further fractions and repeating the process one more time, subjecting the fractions to column chromatography to obtain fractions, concentrating the fractions under reduced pressure to obtain acteoside as residue; and a method of effectively hepatoprotecting a subject using pure Acteoside from plant *Colerbrookea oppositifolia*, said method comprising steps of administering appropriate low-dose of the acteoside to the subject.

14 Claims, 2 Drawing Sheets

US 6,989,162 B2

HEPATOPROTECTIVE AGENT OF PLANT ORIGIN AND A PROCESS THEREOF

FIELD OF THE PRESENT INVENTION

A process of isolation of pure Acteoside of high hepatoprotection from plant *Colebrookea oppositifolia*, said process comprising steps of drying aerial parts of the plant, grounding the dried parts into powder, percolating the powder with water or ethanol for 3–4 times to obtain an extract, filtering the extract for clearing of suspended particles to obtain supernatant, drying the supernatant at about 45 to 55° C. to obtain a residue, fractionating the residue with chloroform, ethyl acetate, and butanol successively, subjecting butanol fraction to adsorption chromatography of $SiO_2$ after adding methanol to the fraction, charging the adsorbed fraction to glass column, eluting the column with solvents of increasing polarity of methanol:chloroform to obtain further fractions and repeating the process one more time, subjecting the fractions to column chromatography to obtain fractions, concentrating the fractions under reduced pressure to obtain acteoside as residue; and a method of effectively hepatoprotecting a subject using pure Acteoside from plant *Colebrookea oppositifolia*, said method comprising steps of administering appropriate low-dose of the acteoside to the subject.

BACKGROUND OF THE PRESENT INVENTION

Phenylethanoids are a class of compounds reported to be present in plants like *Cistanche deserticola* and *Bucldleja* species (Quanbo Xing, Koji Hase et al, *Planta Medica*, 64, 120–125 (1998); Peter J. Houghton and Hiroshi Hikino. *Planta Medica*, Vol. 55, 123–126 (1989).

It is for the first time that a phenylethanoid—verbascoside (also called acteoside or kusaginin) has been isolated by the authors from *Colebrookea oppositifolia* and found to possess a very strong antihepatotoxic/hepatoprotective activity at unusually very low doses (between 1.25 and 2.5 mg/kg) in rats and mice.

The presence of number of flavonoids and glycoflavonoids has already been reported in the literature from *Colebrookea oppositifolia* [S. Aziz Ahmed, S. A. Siddiqui and Asif Zaman, *Indian J. Chemistry* 12 1327–28 (1974); S. A. Patwardhan and A. S. Gupta, *Indian J. Chemistry*, 20B, 627, (1981); Fan Yank, Xing-Li, HAN-Qing Wang and Chong-Ren Yang, *Phytochemistry* 42, 867–69 (1996)]. However, the presence of Acteoside from this plant is being reported for the first time.

Antifertility activity of this plant in male rats with special reference to testicular cell population dynamics have earlier been reported (R. S. Gupta, R. J. Yadav, V. P. Dixit and M. P. Dobhal, *Fitoterapia*, 72, 236–45 (2001).

Though the Hepatoprotective/Antihepatotoxic activity of Acteoside (Verbascoside) isolated from other two plants viz. *Cistanche* species and *Buddleja* species has been reported. (Quanbo Xing, Koji Hase et al, *Planta Medica*, 64, 120–125 (1998); Peter J. Houghton and Hiroshi Hikino. *Planta Medica*, Vol. 55, 123–126 (1989), however the present invention not only reports a distinct source namely *Colebrookea oppositifolia* but the desired activity is accomplished at unusually very low dosage between 1.5 to 2.5 mg/kg in rats.

As already stated above the Hepatoprotective/Antihepatotoxic activity of acteoside has been reported both in vitro and in vivo (Quanbo Xing, Koji Hase et al, *Planta Medica*, 64, 120–125 (1998). But the present invention describes the isolation of acteoside from a hitherto unreported source in such a way that the compound shows antihepatotoxic/hepatoprotective activity at doses nearly 12 to 25 times lower than those already reported in the prior art (Quanbo Xing, Koji Hase et al, *Planta Medica*, 64, 120–125 (1998); Peter J. Houghton and Hiroshi Hikino. *Planta Medica*, Vol. 55, 123–126 (1989). Moreover the parameters evaluated in the prior reports are limited to ALT (in vivo) and AST & MDA (in vitro) whereas the present invention describes the influence of acteoside practically in all important parameters leading to for a clear decision on the efficacy of any hepatoprotective or antihepatotoxic product.

The reason for the activity of acteoside at such low doses compared to the one reported in the prior art may be due to the specific method of its isolation being distinct to yield a product of higher purity. Contaminants in phytochemicals are well documented to seriously jeopardize the activity of pure active compound though there could be synergistic action also of which, however, there in no mention or indication in the prior art.

OBJECTS OF THE PRESENT INVENTION

The main object of the present invention is to isolate a hepatoprotective from plant *Colebrookea oppositifolia*.

Another object of the present invention is to develop a process for the isolation of acteoside from plant *Colebrookea oppositifolia*.

Yet another object of the present invention is to develop a method of hepatoprotecting a subject using *Colebrookea oppositifolia*.

SUMMARY OF THE PRESENT INVENTION

A process of isolation of pure Acteoside of high hepatoprotection from plant *Colebrookea oppositifolia*, said process comprising steps of drying aerial parts of the plant, grounding the dried parts into powder, percolating the powder with water or ethanol for 3–4 times to obtain an extract, filtering the extract for clearing of suspended particles to obtain supernatant, drying the supernatant at about 45 to 55° C. to obtain a residue, fractionating the residue with chloroform, ethyl acetate, and butanol successively, subjecting butanol fraction to adsorption chromatography of $SiO_2$ after adding methanol to the fraction, charging the adsorbed fraction to glass column, eluting the column with solvents of increasing polarity of methanol:chloroform to obtain further fractions and repeating the process one more time, subjecting the fractions to column chromatography to obtain fractions, concentrating the fractions under reduced pressure to obtain acteoside as residue; and a method of effectively hepatoprotecting a subject using pure Acteoside from plant *Colebrookea oppositifolia*, said method comprising steps of administering appropriate low-dose of the acteoside to the subject.

DETAILED DESCRIPTION OF THE PRESENT INVENTION

A process of isolation of pure Acteoside of high hepatoprotection from plant *Colebrookea oppositifolia*, said process comprising steps of drying aerial parts of the plant, grounding the dried parts into powder, percolating the powder with water or ethanol for 3–4 times to obtain an extract, filtering the extract for clearing of suspended particles to obtain supernatant, drying the supernatant at about 45 to 55° C. to obtain a residue, fractionating the residue with chloroform, ethyl acetate, and butanol successively, subjecting butanol fraction to adsorption chromatography of $SiO_2$ after adding methanol to the fraction, charging the adsorbed fraction to glass column, eluting the column with solvents of increasing polarity of methanol:chloroform to obtain further fractions and repeating the process one more time, subjecting the fractions to column chromatography to obtain fractions, concentrating the fractions under reduced pressure to obtain acteoside as residue; and a method of effectively hepatoprotecting a subject using pure Acteoside from plant *Colebrookea oppositifolia*, said method comprising steps of administering appropriate low-dose of the acteoside to the subject.

In an embodiment of the present invention, wherein a process of isolation of pure Acteoside of high hepatoprotection from plant *Colebrookea oppositifolia*, said process comprising steps of:

drying aerial parts of the plant, grounding the dried parts into powder, percolating the powder with water or ethanol for 3–4 times to obtain an extract, filtering the extract for clearing of suspended particles to obtain supernatant, drying the supernatant at about 45 to 55° C. to obtain a residue, fractionating the residue with chloroform, ethyl acetate, and butanol successively, subjecting butanol fraction to adsorption chromatography of $SiO_2$ after adding methanol to the fraction, charging the adsorbed fraction to glass column, eluting the column with solvents of increasing polarity of methanol:chloroform to obtain further fractions and repeating the process one more time, subjecting the fractions to column chromatography to obtain fractions, concentrating the fractions under reduced pressure to obtain acteoside as residue.

In another embodiment of the present invention, wherein the acteoside obtained by the process shows hepatoprotective activity at 12 to 25 times lesser dosage as compared to the one obtained from other sources.

In yet another embodiment of the present invention, wherein the extracts are aqueous and alcoholic extracts.

In still another embodiment of the present invention, wherein acteoside is about 1.0% (wt.) of the total extract.

In still another embodiment of the present invention, wherein a method of effectively hepatoprotecting a subject using pure Acteoside from plant *Colebrookea oppositifolia*, said method comprising steps of administering appropriate low-dose of the acteoside to the subject.

In still another embodiment of the present invention, wherein the dosage is ranging between 0.5 to 10.0 mg/kg body weight.

In still another embodiment of the present invention, wherein acteoside is administered through P.O. routes.

In still another embodiment of the present invention, wherein acteoside reduces the abnormally elevated levels of serum glutamine transferase (GPT).

In still another embodiment of the present invention, wherein acteoside reduces the abnormally elevated levels of serum glutamine transferase (GOT).

In still another embodiment of the present invention, wherein acteoside reduces the abnormally elevated levels of serum alkaline phosphatase (ALP).

In still another embodiment of the present invention, wherein acteoside reduces the abnormally elevated levels of serum Bilirubin.

In still another embodiment of the present invention, wherein acteoside reduces the abnormally elevated levels of serum triglycerides (TG).

In still another embodiment of the present invention, wherein acteoside reduces the abnormally elevated levels of lipid peroxidase (LP).

In still another embodiment of the present invention, wherein acteoside increases the abnormally reduced levels of albumin.

In still another embodiment of the present invention, wherein acteoside increases the abnormally decreased levels of reduced-glutathione.

In still another embodiment of the present invention, wherein acteoside is about 10 to 20 times more effective as compared to commercially available hepatoprotectants.

In still another embodiment of the present invention, wherein acteoside provides about 40–85% protection against hepatotoxicity.

The present invention relates to unusually very low dosage antihepatotoxic/hepatoprotective activity, of a phenylethanoid named as Verbascoside—also termed as Acteoside or Kusaginin isolated and reported for the first time from a plant named *Colebrookea oppositifolia*. The invention describes the isolation of verbascoside in a specific manner and demonstrates antihepatotoxic/hepatoprotective activity at very low doses against different toxins.

The active compound acteoside (verbascoside) is being reported for the first time by the authors of invention from the plant *Colebrookea oppositifolia*. The authenticity of the acteoside isolated by the authors has been confirmed by $^1H$ and $^{13}C$ NMR data similar to reported in literature (*Phytochemistry* 21, 1123–1127 (1982).

BRIEF DESCRIPTION OF THE ACCOMPANYING DRAWINGS

Figure 1:
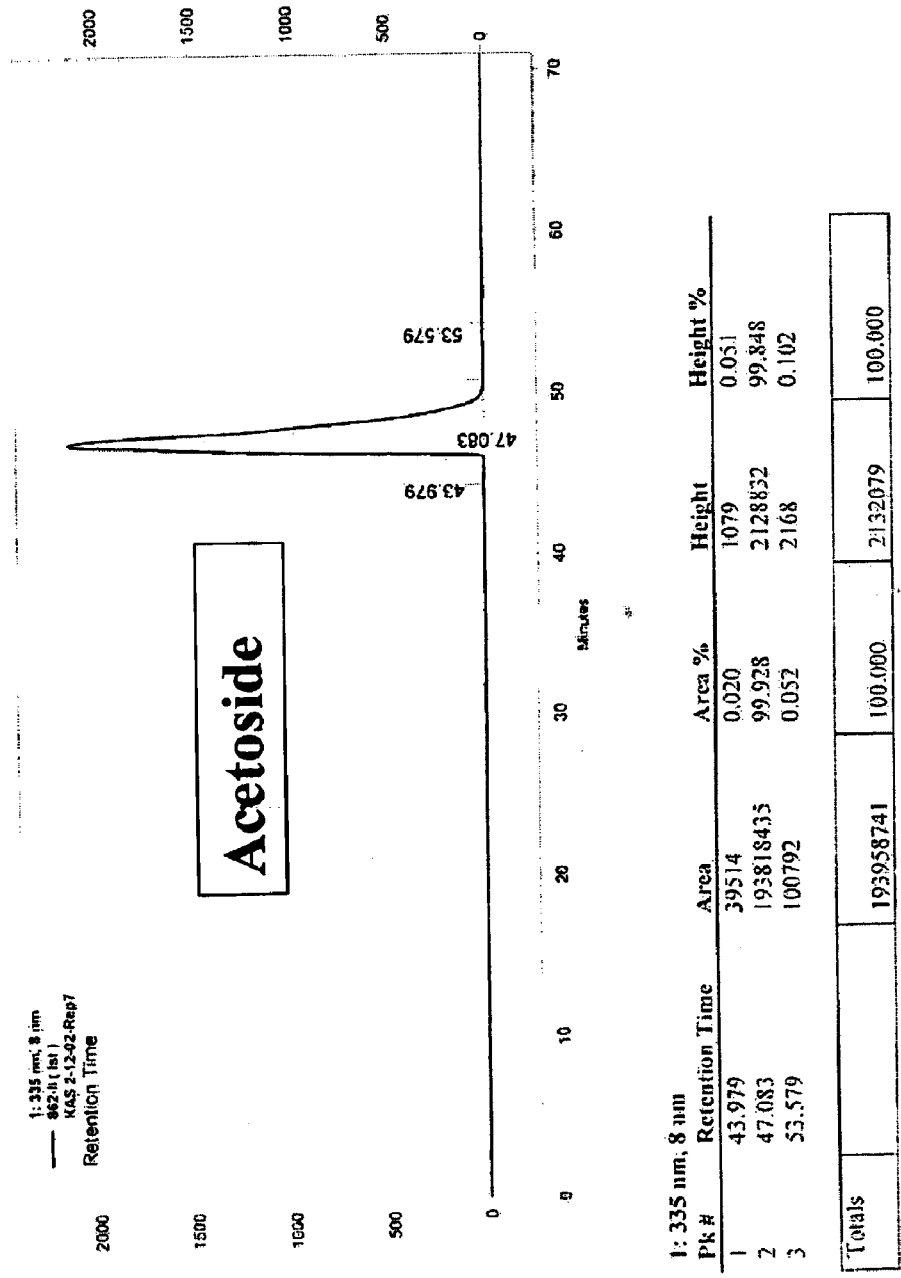
FIG. 1 shows HPLC graph confirming purity.

The process of isolation of acteoside from different extracts (95% alc., 50% alc. and aqueous) of the plant is described in the examples appended herewith as Annexure-1. The HPLC graph confirming purity is enclosed as FIG. 1.

The compound has been bioevaluated for hepatoprotective/antihepatotoxic activity by using a comprehensive study design annexed herewith as Annexure-2. The parameters studied during the bioevaluation to establish the bioefficacy and optimum dose were preferred using the kits (Clonital, Italy and Accurex Biomedical Pvt. Ltd Thane). The list of the parameters is given in Annexure-2 appended herewith. The dose response graphs with respect to different parameters in comparison with the standard drug with silymarin and glycyrrhizin are given in Annexure-3 appended herewith.

Figure 2:
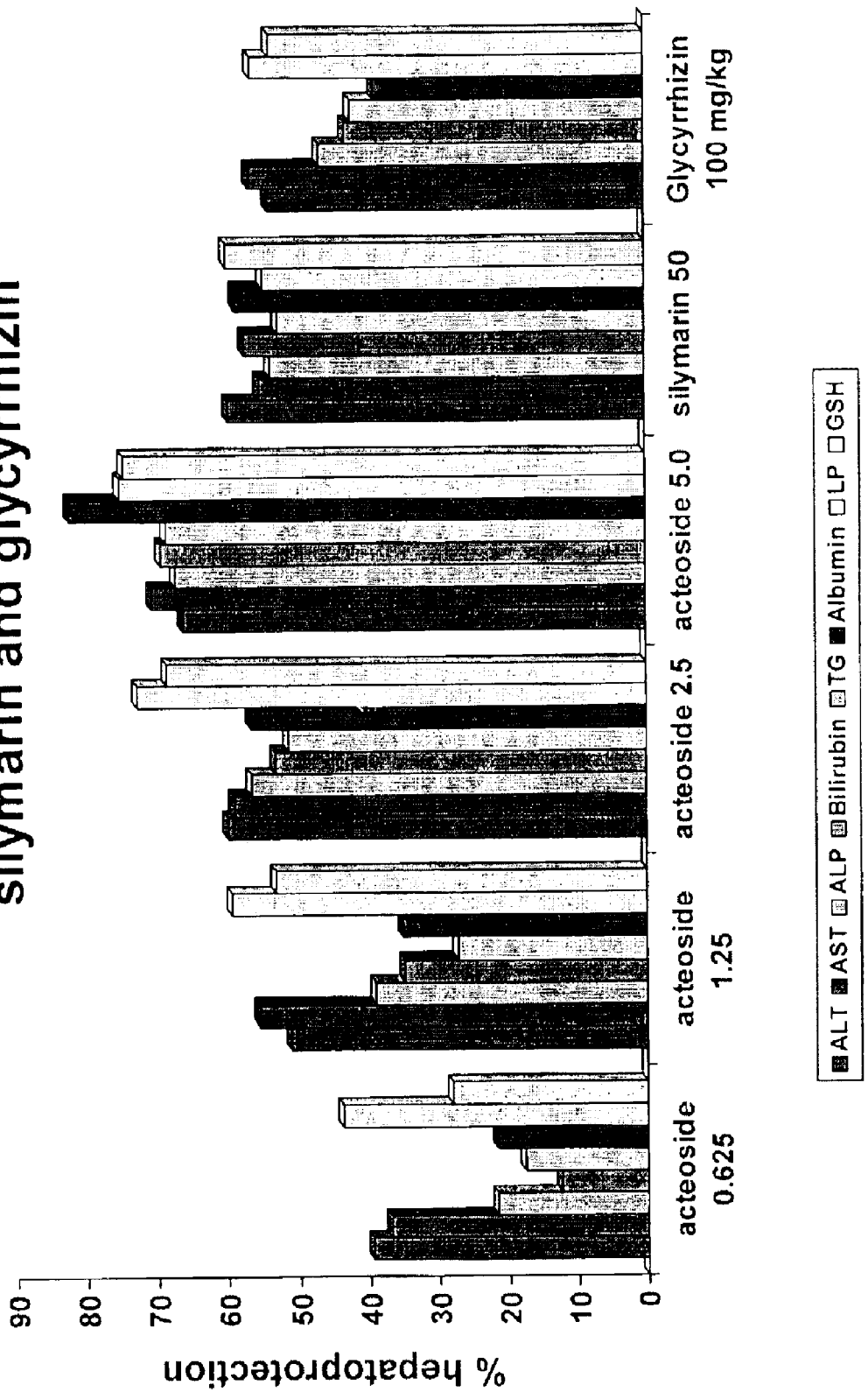
FIG. 2 shows comparative hepatoprotective activity (%) of acteoside, silymarin, and glycyrrhizia.

The bioevaluation data for each dose of the acteoside as compared to reference materials viz. silymarin, glycyrrhizin, and required controls are given in the Table-1 which is appended herewith the invention. As is clear from the FIG. 2 and Table-1 all the parameters which were compromised after the administration of hepatotoxin $CCl_4$ have a very good tendency to revert back to normal levels from a dose of 1.25 mg upto 5 mg/kg of acteoside. The overall percent protection provided by acteoside with reference to all the parameters studied in the invention is generally from 40–80%, and is better than that rendered by silymarin even at 10–20 times the dosage of acteoside.

The optimum dose to achieve this protection with acteoside of the invention lies between 1.25 mg/kg and 2.5 mg/kg. Statistically, there is no significance observed between the three doses viz. 1.25, 2.5 and 5 mg/kg except when 1.25 mg/kg dose data is compared with that of 5 mg/kg dose (Table-2). But no statistical significance is observable between higher doses i.e. 2.5 mg/kg and 5 mg/kg. At the same time, similar observation holds fully well for dose effect between 1.25 and 2.5 mg/kg.

The above-stated invention is elaborated in the form of examples and should not be construed to limit the scope of the invention

EXAMPLE 1

Dried aerial parts of plant material *Colebrookea oppositifolia* (500 gm) were ground to a coarse powder. The powder was percolated with 95% ethanol for fourteen hours. Extraction process was repeated four times using total of 9 litres of 95% ethanol (3.0+2.0+2.0+2.0 Litre, four extractions). All the four extracts were pooled and filtered clear of suspended particles. The supernatant was evaporated to dryness on a wiped film evaporator at 50±5° C. Residue obtained was 60.0 g, (coded as RJM/0862/P08/A001) extractive value 12%.

The extract was fractionated with $CHCl_3$, EtOAc and n-BuOH (2×1 Litre each) successively. 15.0 g n-BuOH extract was subjected to adsorption chromatography after dissolving in minimum quantity of MeOH, and adsorbing on $SiO_2$ gel, 100–200 mesh (100 gm.) Solvent was completely removed to get free flowing material. The adsorbed extract was charged in a glass column of 37.5 mm Ø. The column was eluted with solvents by gradually increasing the % age of MeOH in $CHCl_3$ 105 fractions of 100 ml each were collected and pooled on the bases of TLC patterns checked by using EtOAc:HCOOH:$H_2O$::8:1:1 as mobile phase. Spots were visualised by spraying with freshly prepared Borinate-PEG 4000 solution [1% solution of 2-aminoethyldiphenylborinate in MeOH and 5% solution of polyethylene glycol 4000 in EtOH (mixed 1:1 v/v before spraying)].

Seven of the fractions showing same TLC pattern were pooled, dried and subjected to rechromatography using 100–200 mesh $SiO_2$ gel column (1:20 ratio) and eluted with $CHCl_3$:MeOH mixtures of increasing polarity. In all 60 fractions of 200 ml each were collected. Eight of the fractions were pooled on the bases of TLC were dried and again subjected to column chromatography. 30 fractions of 100 ml each were collected. Six fractions were concentrated under reduced pressure. Residue was crystallised from MeOH/$CHCl_3$ as a colourless amorphous powder, soluble in McOH . Compound found at Rf 0.42, (solvent system EtOAc:HCOOH:$H_2O$::8:1:1) was coded as 862-II . The purity of 862-II was established on the basis of HPLC using following operating conditions.

| Column | RP-18e (E-Merck, 5 μm, 4.6 × 250 mm), at |
|---|---|
| Mobile Phase | Acetonitrile (B): 1.5% acetic acid in water (A) |
| Flow rate | 1 ml/min. |
| λmax | 335 nm |

The compound was established as Verbascoside on the basis of NMR ($^1H$ and $^{13}C$) and FABMS data.

EXAMPLE 2

Dried aerial parts (500 gm) of *Colebrookea oppositifolia* were ground and percolated with 50% aqueous ethanol four times (50% EtOH, 4×2.5 Litre) for 14 hrs each. All the four extracts were pooled. The pooled aqueous extracts were centrifuged, clear supernatant was evaporated to dryness on a wiped film evaporator at 50±5° C. The residue (90 g) was coded as RJM/0862/P08/A002 (extractive value 18%) and fractionated with $CHCl_3$, EtOAc and n-BuOH successively.

The n-BuOH ext. was chromatographed on a column of silica gel (60–120 mesh) eluted with a gradient of MeOH in $CHCl_3$. The $CHCl_3$:MeOH (5:1) eluate was rechromatographed on a silica gel (100–200 mesh) column using $CHCl_3$-MeOH:$H_2O$ (6:1:0.1) as solvent. Fractions homogeneous on TLC were pooled, dried and charged on a sephadex LH-20 column, eluted with MeOH to produce two fractions of 500 ml each. Second fraction containing mainly the target compound (862-II) was subjected to further purification over a sephadex LH-20. Column was eluted with MeOH:$H_2O$ (3:2) to afford a fraction, which on crystallisation from MeOH/$CHCl_3$ yielded a colourless amorphous powder soluble in MeOH , Rf 0.42 (solvent system EtOAc:HCOOH:$H_2O$::8:1:1).

Standardisation of the extract RJM/0862/P08/A002 was carried out on the basis of 862-II by HPLC using following operating conditions:

| Column | RP-18e (E-Merck, 5 μm, 4.6 × 250 mm), at |
|---|---|
| Mobile Phase | Acetonitrile (B): 1.5% acetic acid in water (A) |
| Flow rate | 1 ml/min. |
| λmax | 335 nm |

The compound was established as Verbascoside on the basis of NMR ($^1H$ and $^{13}C$) and FABMS data.

The % age of 862-II in the extract RJM/0862/P08/A002 was found to be 0.86.

EXAMPLE 3

*Colebrookea oppositifolia* aerial parts (500 g) were ground to a coarse powder and then extracted with deionised water at 98±1° C. for 2 hrs. Extraction process was repeated four times using total water (1+3×0.7 Litre, four extractions). All the four extracts were pooled The pooled extract was centrifuged, the cleat filtrate was lyophilized to get light yellow amorphous powder (yield 95 gm). Aqueous extract residue and coded as RJM/0862/P08/A003 (extractive value 19%) was fractionated with $CHCl_3$, EtOAc and n-BuOH successively.

n-BuOH extract was subjected to adsorption chromatography on $SiO_2$ gel, 60–120 mesh (150 gm). Solvent was completely removed to get free flowing material. A glass column of 1.5 inch dia was packed with 100 gm $SiO_2$ gel, 60–120 mesh in EtOAc. The adsorbed material was charged in the column. The column was eluted with EtOAc and by gradually increasing the % age with MeOH . In all 120 fractions of 100 ml each were collected and pooled on the basis of TLC pattern (EtOAc:HCOOH:$H_2O$::8:1:1 as developing solvent). Spots were visualised by spraying with freshly prepared Borinate-PEG 4000 solution [1% solution of 2-aminoethyldiphenylborinate in MeOH and 5% solution of polyethylene glycol 4000 in EtOH (mixed 1:1 v/v before spraying)].

Fractions eluted in EtOAc and 10% MeOH showed same TLC pattern. These fractions were pooled, dried and then dissolved in minimum quantity of MeOH . Crystallisation was carried out by the addition of $CHCl_3$ in small portions to methanol solution which yielded a colourless amorphous powder characterised as 862-II.

Standardisation of the extract RJM/0862/P08/A003 was carried out on the basis of 862-II by HPLC using following operating conditions:

| | |
|---|---|
| Column | RP-18e (E-Merck, 5 µm, 4.6 × 250 mm), at |
| Mobile Phase | Acetonitrile (B): 1.5% acetic acid in water (A) |
| Flow rate | 1 ml/min. |
| λmax | 335 nm |

The compound was established as Verbascoside on the basis of NMR ($^1$H and $^{13}$C) and FABMS data.

The % age of 862-II in the extract RJM/0862/P08/A003 was found to be 0.22. 862-II, amorphous powder, mp 145–146° C., $[\alpha]^{21}$ –85.6 [C 0.5% MeOH], MS:FABMS, [M+Na]$^+$ m/z 647 was found to be a known Phenyl propanoid i.e., Verbascoside (Acteoside); [β-(3',4'-dihydroxyphenyl) ethyl —O-α-L-rhamnopyranosyl (1→3)-β-D-(4-O-caffeoyl)-glucopyranoside]. Structure was finally confirmed by $^1$H and $^{13}$CNMR data similar to that reported in literature (Andary C., Wylde, R. Laffite C., Privat G. and Winternitz F.; Laboratie de Botanique et Cryptogamie, Faculte de Pharmacie. 34000 Montpellier. France; Phytochemistry, 21 (5), 1123–1127 (1982).

STUDY DESIGN

| | |
|---|---|
| 1. Animals | Albino rats (Wistar, 150–180 g) either sex |
| | Albino mice (Swiss, 25–30 g) either sex |
| 2. Hepatotoxin | Carbon tetrachloride (CCl$_4$) |
| 3. Study | Prophylactic |
| 4. Treatment Schedule | 48 h, 24 h, 02 h, before and 06 h after toxin; blood & liver samples collection 18 h after last treatment of test material/reference standard. |
| 5. Doses | |
| Acteoside | 0.625, 1.25, 2.5 & 5.0 mg/kg, p.o. |
| Silymarin | 50 mg/kg, p.o. |
| Glycyrrhizin | 100 mg/kg, p.o. |
| CCl$_4$ | 1 ml/kg p.o. in liquid paraffin (1:1) |
| 6. Parameters | |
| Serum | |
| Bilirubin: | Jendrassik Method by using Kit supplied by Clonital, 24030-Carvico (BG)-Italy. |

-continued
STUDY DESIGN

| | |
|---|---|
| Triglycerides: | Enzymatic GPO-POD Method by the Kit supplied by Accurex BiomedicalPvt. Ltd., Thane |
| Albumin: | Colorimetric B.C.G. Method by the Kit supplied by Accurex Biomedical Pvt. Ltd., Thane |
| Transaminases | (ALT, & AST): Pyruvate formed by transamination reaction was determined spectrophotometrically after reaction with 2,4-dinitrophenylhydrazine (Reitman and Frankel, 1957). |
| ALP: | p-nitrophenol formed in alkaline medium was measured spectrophotometrically using p-nitrophenyl phosphate as substrate (Waler and Schutt, 1974). |
| Liver Homogenate: | |
| GSH: | It was determined after deproteination by reaction with DTNB (Ellman 1959 as modified by David 1987). |
| Lipid peroxidation: | Thiobarbituric acid reacting substances were determined spectrophotometrically at 535 nm. By the method of Buege and Aust (1978). |

Hepatoprotective activity:

Hepatoprotective activity (H) was calculated by the following equation:

$$H = [1 - (TC - V/VC - V)] \times 100$$

Where TC, VC, and V are drug+toxin, vehicle+toxin and vehicle treated groups of animals respectively.

TABLE 1

Hepatoprotective potential of Acteoside against CCl$_4$ induced hepatic injury in Rodents Prophylactic).

| Treatment | Dose mg/kg | GPT (Units) | GOT (Units) | ALP[b] | Bilirubin (mg %) | TG (mg %) | Albumin (g %) | LP[c] | GSH[d] |
|---|---|---|---|---|---|---|---|---|---|
| Vehicle | — | 90.76 ± 8.49 | 99.26 ± 7.62 | 31.72 ± 1.63 | 0.27 ± 0.02 | 30.14 ± 2.58 | 4.16 ± 0.17 | 30.90 ± 1.62 | 8.31 ± 0278 |
| Veh + CCl$_4$ | — | 1513.17 ± 94.21 | 1006.20 ± 33.43 | 76.40 ± 3.68 | 0.76 ± 0.02 | 90.85 ± 4.12 | 2.76 ± 0.11 | 84.35 ± 3.97 | 3.25 ± 0.17 |
| Acteoside only (Per-se) | 5 | 98.91 ± 5.30 | 94.71 ± 5.29 | 31.87 ± 2.15 | 0.27 ± 0.02 | 31.10 ± 2.39 | 4.66 ± 0.18 | 30.52 ± 1.38 | 8.33 ± 0.33 |
| Acteoside + CCl$_4$ | 0.625 | 852.27 ± 47.93 (39.44) | 673.82 ± 56.28 (36.64) | 66.80 ± 3.53 (21.48) | 0.70 ± 0.03 (12.24) | 80.15 ± 3.53 (17.63) | 3.06 ± 0.07 (21.43) | 61.08 ± 3.39 (43.53) | 4.66 ± 0.28 (27.86) |
| Acteoside + CCl$_4$ | 1.25 | 787.56 ± 57.49 (51.01) | 503.42 ± 48.95 (55.43) | 59.10 ± 3.09 (38.72) | 0.59 ± 0.03 (34.69) | 74.38 ± 3.78 (27.13) | 3.25 ± 0.14 (35.00) | 52.61 ± 2.25 (59.38) | 5.93 ± 0.32 (52.96) |
| Acteoside + CCl$_4$ | 2.5 | 662.62 ± 39.80 (59.79) | 471.81 ± 26.40 (58.92) | 51.20 ± 1.42 (56.40) | 0.50 ± 0.03 (53.06) | 59.85 ± 1.88 (51.06) | 3.55 ± 0.22 (56.43) | 45.46 ± 2.79 (72.76) | 6.72 ± 0.28 (68.57) |
| Acteoside + CCl$_4$ | 5.0 | 573.10 ± 28.25 (66.08) | 366.89 ± 26.97 (70.49) | 46.37 ± 1.89 (67.21) | 0.42 ± 0.02 (69.38) | 49.31 ± 1.47 (68.42) | 3.91 ± 0.12 (82.14) | 44.22 ± 1.66 (75.07) | 7.02 ± 0.46 (74.50) |

TABLE 1-continued

Hepatoprotective potential of Acteoside against CCl₄ induced hepatic injury in Rodents Prophylactic).

| | | Serum parameter[a] | | | | | | Hepatic parameters | |
|---|---|---|---|---|---|---|---|---|---|
| Treatment | Dose mg/kg | GPT (Units) | GOT (Units) | ALP[b] | Bilirubin (mg %) | TG (mg %) | Albumin (g %) | LP[c] | GSH[d] |
| Silymarin + CCl₄ | 50 | 665.48 ± 50.08 (59.59) | 506.88 ± 31.82 (55.06) | 52.47 ± 2.43 (53.56) | 0.48 ± 0.02 (57.14) | 58.94 ± 3.35 (52.56) | 3.55 ± 0.22 (58.57) | 55.23 ± 4.66 (54.48) | 6.28 ± 0.32 (59.88) |
| Glycyrrhizin + CCl₄ | 100 | 746.87 ± 49.77 (53.87) | 494.27 ± 36.28 (56.44) | 55.63 ± 3.52 (46.48) | 0.55 ± 0.04 (42.85) | 65.31 ± 3.69 (42.07) | 3.30 ± 0.12 (38.57) | 54.37 ± 4.82 (56.08) | 5.96 ± 0.26 (53.55) |

[a]Values represent mean ± SE of six animals in each group;
Units: Each unit is $\mu$ mole pyruvate/min/L;
[b]$\mu$ mole of p-nitrophenol formed/min/L
[c]lipid peroxidation (n mole MDA/g liver); d: glutathione ($\mu$ mole GSH/g liver).
Ö: Within parenthesis % protection
Ö: There is no effect on BP and Respiration in the doses of 30 $\mu$g, 100 $\mu$g, 300 $\mu$g and 1 mg I.V. in rat as there is no change in base line.
Ö: There is no change in the base line against the Histamine, 5-HT and Acetylcholine induced contraction on the isolated rat colon.

TABLE 2

Significance analysis between the doses of acteoside
(1.25, 2.5 and 5.0 mg/kg, p.o. at Df. 10 (Student t test)

| | | Serum parameter[a] | | | | | | Hepatic parameters | |
|---|---|---|---|---|---|---|---|---|---|
| Dose:Dose | Student t test analysis | GPT (Units) | GOT (Units) | ALP[b] | Bilirubin (mg %) | TG (mg %) | Albumin (g %) | LP[c] | GSH[d] |
| 1.25:2.5 (a:b) | t value P value* | 1.78 <0.20[NS] | 0.56 <0.20[NS] | 2.32 <0.05 | 2.12 <0.10[NS] | 3.44 <0.01 | 1.44 <0.10[NS] | 1.99 <0.10[NS] | 1.85 <0.10[NS] |
| 1.25:5.0 (a:c) | t value P value* | 3.34 <0.01 | 2.44 <0.05 | 3.51 <0.01 | 4.71 <0.001 | 6.18 <0.001 | 3.58 <0.01 | 3.00 <0.01 | 1.94 <0.10[NS] |
| 2.5:5.0 (b:c) | t value P value* | 1.83 <0.10[NS] | 2.78 <0.02 | 2.04 <0.01[NS] | 2.22 <0.05 | 4.41 <0.01 | 1.43 <0.10[NS] | 0.38 <0.10[NS] | 0.55 <0.10[NS] |

[a]Values represent mean ± SE of six animals in each group;
Units: Each unit is $\mu$ mole pyruvate/min/L;
[b]$\mu$ mole of p-nitrophenol formed/min/L
[c]lipid peroxidation (n mole MDA/g liver);
[d]glutathione ($\mu$ mole GSH/g liver).
*p < 0.05,
**p < 0.01, P < 0.001, p > 0.05, [not significant] Student t test between the respective does.

What is claimed is:

1. A process of isolation of acteoside of high hepatoprotection from the plant *Colebrookea coppositifolia*, said process comprising steps of:
    a. drying aerial parts of the plant,
    b. grounding the dried parts into powder,
    c. percolating the powder with water or ethanol for 3–4 times to obtain an extract,
    d. filtering the extract for clearing of suspended particles to obtain supernatant,
    e. drying the supernatant at about 45 to 55° C. to obtain a residue,
    f. fractionating the residue with chloroform, ethyl acetate, and butanol successively,
    g. subjecting the butanol fraction to adsorption chromatography of SiO₂ after adding methanol to the fraction,
    h. charging the adsorbed fraction to a glass column,
    i. eluting the column with solvents of increasing polarity of methanol:chloroform to obtain further fractions and repeating the process one more time,
    j. subjecting the fractions to column chromatography to obtain additional fractions,
    k. concentrating the additional fractions under reduced pressure to obtain acteoside as a residue.

2. A process as claimed in claim 1, wherein the extract is aqueous and alcoholic.

3. A process as claimed in claim 1, wherein the extract comprises about 1.0% by weight acteoside.

4. A method of effectively hepatoprotecting a subject using pure acteoside from plant *Colebrookea oppositifolia*, said method comprising steps of administering acteoside to the subject in a dose ranging from 1.25 to 5 mg/kg body weight.

5. A method as claimed in claim 4, wherein the acteoside is administered through P.O. routes.

6. A method as claimed in claim 4, wherein the acteoside reduces abnormally elevated levels of serum glutamine transferase (GPT).

7. A method as claimed in claim 4, wherein the acteoside reduces abnormally elevated levels of serum glutamine transferase (GOT).

8. A method as claimed in claim 4, wherein the acteoside reduces abnormally elevated levels of serum alkaline phosphatase (ALP).

9. A method as claimed in claim 4, wherein the acteoside reduces abnormally elevated levels of serum Bilirubin.

10. A method as claimed in claim 4, wherein the acteoside reduces abnormally elevated levels of serum triglycerides (TG).

11. A method as claimed in claim 4, wherein the acteoside reduces abnormally elevated levels of lipid peroxidase (LP).

12. A method as claimed in claim 4, wherein the acteoside increases abnormally reduced levels of albumin.

13. A method as claimed in claim 4, wherein the acteoside increases abnormally decreased levels of reduced-glutathione.

14. A method as claimed in claim 4, wherein the acteoside provides protection against hepatotoxicity.

* * * * *